(12) United States Patent
Cuenoud et al.

(10) Patent No.: US 6,921,757 B2
(45) Date of Patent: Jul. 26, 2005

(54) ORGANIC COMPOUNDS

(75) Inventors: Bernard Cuenoud, Horsham (GB); David Beattie, Horsham (GB); Thomas Hugo Keller, Horsham (GB); Gaynor Elizabeth Pilgrim, Horsham (GB); David Andrew Sandham, Horsham (GB); Simon James Watson, Horsham (GB)

(73) Assignee: Novartis AG, Basel (CH)

( * ) Notice: Subject to any disclaimer, the term of this patent is extended or adjusted under 35 U.S.C. 154(b) by 13 days.

(21) Appl. No.: 10/312,021

(22) PCT Filed: Jun. 26, 2001

(86) PCT No.: PCT/EP01/07249

§ 371 (c)(1),
(2), (4) Date: Dec. 20, 2002

(87) PCT Pub. No.: WO02/00679

PCT Pub. Date: Jan. 3, 2002

(65) Prior Publication Data

US 2003/0158163 A1 Aug. 21, 2003

(30) Foreign Application Priority Data

Jun. 28, 2000 (GB) .............................................. 0015876

(51) Int. Cl.[7] ........................ A61K 31/56; A61K 31/58; C07J 3/00; C07J 17/00; C07J 43/00
(52) U.S. Cl. ........................ 514/172; 514/176; 514/180; 540/2; 540/108; 540/110; 540/113; 540/114; 540/116; 552/610
(58) Field of Search .................................. 514/172, 176, 514/180; 540/2, 108, 110, 113, 114, 116; 552/610

(56) References Cited

U.S. PATENT DOCUMENTS

| 3,639,434 A | | 2/1972 | Oxley et al. | |
| 3,828,080 A | * | 8/1974 | Phillipps et al. | ............. 552/610 |
| 3,856,828 A | * | 12/1974 | Phillipps et al. | ............. 552/528 |
| 4,226,862 A | * | 10/1980 | Riva et al. | .................. 514/174 |
| 4,285,937 A | | 8/1981 | Kalvoda | |
| 4,607,028 A | * | 8/1986 | Schmidlin | .................. 514/180 |

FOREIGN PATENT DOCUMENTS

| EP | 0 057 401 | * 8/1982 |
| EP | 0 135 476 | 3/1985 |
| GB | 1 384 372 | 2/1975 |
| WO | WO 95 20393 | 1/1995 |

OTHER PUBLICATIONS

Ikegami et al., "Pharmaceutical Preparations Containing Steroid and Manufacture Thereof", Chemical Abstracts Service, Accession No. 126:79939 (abstract) & JP 08 291073 A (Nov. 5, 1996).

Ikegami et al., "Crystals of a Steroid for Powdered Preparation for Inhalants and Manufacture Thereof", Chemical Abstracts Service, Accession No. 126:79938 (abstract) & JP 08 291072 A (Nov. 5, 1996).

Isogai et al., "Binding Affinities of Mometasone Furoate and Related Compounds Including Its Metabolites for the Glucocorticoid Receptor of Rat Skin Tissue", Journal of Steroid Biochemistry and Molecular Biology, vol. 44, No. 2 pp. 141–145, (1993).

Shapiro et al., "17 Heteroaroyl Esters of Corticosteroids 2. 11 Beta Hyroxy Series", Journal of Medicinal Chemistry, American Chemical Society, vol. 30, No. 9, pp. 1581–1588, (1987).

Shapiro et al., "Synthesis and Structure–Activity Studies of Corticosteroid 17. Heterocyclic Aromatic Esters 1. 9–Alpha 11 Beta Dichloro Series", Journal of Medicinal Chemistry, vol., 30, No. 6, pp. 1068–1073, (1987).

* cited by examiner

Primary Examiner—Barbara P. Badio
(74) Attorney, Agent, or Firm—Gregory C. Houghton; Susan L. Hess

(57) ABSTRACT

Compounds of formula (I), where R is a monovalent cyclic organic group having from 3 to 15 atoms in the ring system, useful as pharmaceuticals

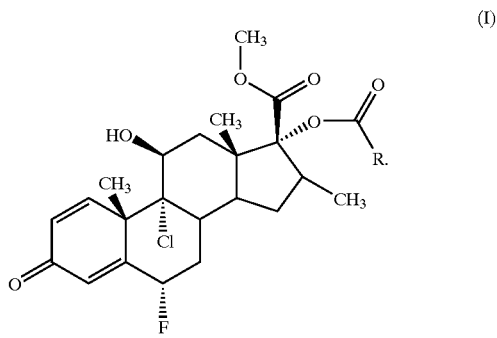

20 Claims, No Drawings

ORGANIC COMPOUNDS

This Application is a 371 of PCT/EPO1/07249 filed on Jun. 26, 2001.

This invention relates to organic compounds, their preparation and their use as pharmaceuticals In one aspect, the present invention provides compounds of formula

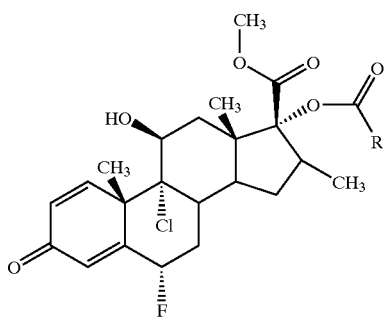

I where R is a monovalent cyclic organic group having from 3 to 15 atoms in the ring system.

Terms used in the specification have the following meanings:

"$C_1$–$C_4$-alkyly" denotes straight chain or branched $C_1$–$C_4$-alkyl, which may be methyl, ethyl, n-propyl, isopropyl, n-butyl, sec-butyl, iso-butyl or tert-butyl.

"$C_1$–$C_4$-alkylamino" denotes amino substituted by $C_1$–$C_4$-alkyl as hereinbefore defined.

"(Di-$C_1$–$C_4$-alkyl)amino" denotes amino disubstituted by $C_1$–$C_4$-alkyl as hereinbefore defined.

"$C_1$–$C_4$-alkylsulfonyl" denotes sulfonyl substituted by $C_1$–$C_4$-alkyl as hereinbefore defined.

"Halo-$C_1$–$C_4$-alkyl" denotes $C_1$–$C_4$-alkyl as hereinbefore defined substituted by one or more, preferably one, two or three halogen atoms, preferably fluorine or chlorine atoms.

"Hydroxy-$C_1$–$C_4$-alkyl" denotes $C_1$–$C_4$-alkyl as hereinbefore defined substituted by one or more, preferably one, two or three hydroxy groups.

"$C_1$–$C_4$-alkoxy" denotes straight chain or branched $C_1$–$C_4$-alkoxy and may be methoxy, ethoxy, n-propoxy, isopropoxy, n-butoxy, isobutoxy, sec-butoxy or tert-butoxy.

"$C_1$–$C_4$-alkoxycarbonyl" denotes carbonyl substituted by $C_1$–$C_4$-alkoxy as hereinbefore defined and may be methoxy-, ethoxy-, n-propoxy-, isopropoxy-, n-butoxy-, isobutoxy-, sec-butoxy- or tert-butoxycarbonyl.

"$C_1$–$C_4$-alkylthio" denotes straight chain or branched $C_1$–$C_4$-alkylthio and may be methylthio, ethylthio, n-propylthio, isopropylthio, n-butylthio, isobutylthio, sec-butylthio or tert-butylthio.

"$C_1$–$C_4$-acyl" denotes carbonyl substituted by $C_1$–$C_4$-alkyl as hereinbefore defined "$C_1$–$C_4$-acyloxy" denotes carbonyloxy substituted by $C_1$–$C_4$-alkyl as hereinbefore defined.

"$C_1$–$C_4$-acylamino" denotes amino substituted by formyl or $C_1$–$C_4$ acyl as hereinbefore defined.

R may be a carbocyclic group or a heterocyclic group having one or more ring hetero atoms selected from nitrogen, oxygen and sulfur. In one embodiment, R is a cycloaliphatic group having 3 to 8 carbon atoms, for example $C_3$–$C_8$-cycloalkyl such as cyclopropyl, methylcyclopropyl, cyclobutyl, methylcyclobutyl, cyclopentyl, cyclohexyl, methylcyclohexyl, dimethylcyclohexyl or cycloheptyl, preferably $C_3$–$C_6$-cycloalkyl.

In another embodiment, R is an at least partially saturated heterocyclic group having 5 to 10 ring atoms, of which one or more are ring hetero atoms selected from nitrogen, oxygen and sulfur, preferably having 5 to 7 ring atoms, of which one or two are hetero atoms selected from nitrogen and oxygen, especially a 5-membered heterocyclic group having one ring hetero atom, such as a tetrahydrofuryl or oxotetrahydrofuryl group.

In a further embodiment, R is a carbocyclic or heterocyclic aromatic group having 5 to 15 atoms in the ring system. For example, R may be such an aromatic group in which the ring system is unsubstituted or is substituted by one or more substituents selected from halogen, cyano, $C_1$–$C_4$-alkyl, halo-$C_1$–$C_4$-alkyl, $C_1$–$C_4$-alkoxy, $C_1$–$C_4$-alkylthio, hydroxyl, $C_1$–$C_4$-acyl, $C_1$–$C_4$-acyloxy, amino, $C_1$–$C_4$-alkylamino, di-($C_1$–$C_4$-alkyl)amino, $C_1$–$C_4$-acylamino, $C_1$–$C_4$-acyl($C_1$–$C_4$-alkyl)amino, $C_1$–$C_4$-alkylsulfonyl ($C_1$–$C_4$-alkyl)amino, $C_1$–$C_4$-alkoxycarbonyl, or 5-membered heterocyclyl, usually N-heterocyclyl having one or two nitrogen atoms. One preferred class of such aromatic groups is phenyl or naphthyl optionally substituted by one or more, preferably one, two or three, substituents selected from cyano, $C_1$–$C_4$-alkyl, halo-$C_1$–$C_4$-alkyl, $C_1$–$C_4$ alkoxy, halogen, hydroxyl, $C_1$–$C_4$-acyloxy, amino, $C_1$–$C_4$-alkylamino, di-$C_1$–$C_4$-alkylamino, $C_1$–$C_4$-acylamino, $C_1$–$C_4$-acyl($C_1$–$C_4$ alkyl)amino, $C_1$–$C_4$ alkylsulfonyl ($C_1$–$C_4$alkyl)amino or $C_1$–$C_4$ alkoxycarbonyl, especially preferred such aromatic groups including phenyl, cyanophenyl, tolyl, dimethylphenyl, ethylphenyl, (trifluoromethyl)phenyl, dimethoxyphenyl, diethoxyphenyl, hydroxyphenyl, (methylamino)phenyl, (methanesulfonyl-methylamino)phenyl and (methoxycarbonyl)phenyl.

Another preferred class of such aromatic groups is a heterocyclic aromatic group having a 6-membered heterocyclic ring with one, two or three ring heteroatoms, preferably nitrogen, the heterocyclic ring being unsubstituted or substituted by one or more, preferably one, two or three, substituents selected from halogen, cyano, hydroxyl, $C_1$–$C_4$-acyloxy, amino, $C_1$–$C_4$ alkylamino, di-($C_1$–$C_4$-alkyl)amino, $C_1$–$C_4$-alkyl, hydroxy-$C_1$–$C_4$-alkyl, halo-$C_1$–$C_4$-alkyl, $C_1$–$C_4$-alkoxy, or $C_1$–$C_4$-alkylthio, and the heterocyclic ring being optionally fused to a benzene ring. Preferred such heterocyclic aromatic groups include those in which the heterocyclic group has one or two nitrogen atoms in the ring, especially a pyridine, pyrimidine, pyrazine or pyridazine ring. Especially preferred heterocyclic aromatic groups are pyridyl, pyrimidyl and pyrazinyl groups, optionally substituted by one or two substituents selected from halogen (particularly chlorine) or $C_1$–$C_4$-alkyl (especially methyl or n-butyl).

Another preferred class of such aromatic groups is a heterocyclic aromatic group having a 5-membered heterocyclic ring with one, two or three ring hetero atoms selected from nitrogen, oxygen and sulfur, the heterocyclic ring being unsubstituted or substituted by one or two substituents selected from halogen, $C_1$–$C_4$-alkyl, halo-$C_1$–$C_4$-alkyl, $C_1$–$C_4$-alkoxy, $C_1$–$C_4$-alkylthio, cyano or hydroxy-$C_1$–$C_4$-alkyl and the heterocyclic ring being optionally fused to a benzene ring. Preferred such heterocyclic aromatic groups include those in which the heterocyclic ring has one nitrogen, oxygen or sulfur atom in the ring or one oxygen and one or two nitrogen atoms in the ring, or one sulfur and one or two nitrogen atoms in the ring, especially a pyrrole, furan, thiophene, oxazole, isoxazole, imidazole, pyrazole, furazan, thiazole or thiadiazole ring. Especially preferred heterocyclic aromatic groups are pyrrolyl, furyl and thienyl groups optionally substituted by one or two substituents selected from halogen (particularly chlorine or bromine), $C_1$–$C_4$-alkyl (particularly methyl or ethyl), halo-$C_1$–$C_4$-alkyl (particularly trifluoromethyl), $C_1$–$C_4$-alkoxy (particularly methoxy), $C_1$–$C_4$-alkylthio (particularly methylthio), cyano or hydroxy-$C_1$–$C_4$-alkyl (particularly hydroxymethyl); isoxazolyl, imidazolyl, pyrazolyl, thiazolyl or thiadiazolyl groups optionally substituted by one or two $C_1$–$C_4$-alkyl groups; and benzofuryl, benzothienyl and benzofurazanyl groups.

In compounds of formula I, the indicated methyl group in the 16 position of the corticosteroid ring system may be in the alpha or beta conformation. 16-α-methyl compounds are preferred.

Compounds of formula I in which R contains a basic group are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-rboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

Especially preferred compounds of formula I include those hereinafter described in the Examples, particularly those of Examples 3, 11, 14, 17, 19, 26, 34, 37, 39, 51, 60, 67, 72, 73, 90, 99 and 101.

In another aspect, the present invention provides a process for the preparation of compounds of formula I which comprises (A) conversion of a carboxylic acid of formula

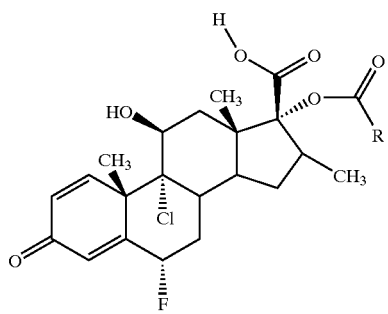

II where R is as hereinbefore defined, or an ester-forming functional derivative thereof, into the methyl ester thereof; or (B) hydrochlorination of a compound of formula

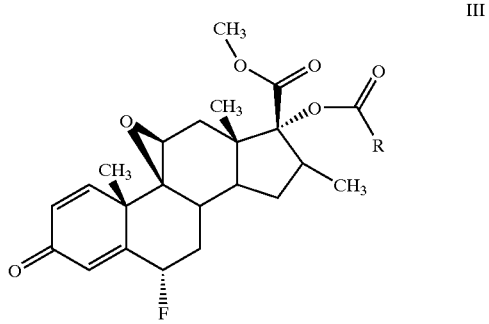

III where R is as hereinbefore defined.

Process variant (A) may be carried out using known procedures for converting a carboxylic acid, or ester-forming functional derivative thereof such as an acid halide thereof, into the corresponding methyl ester. Conveniently, the carboxylic acid is reacted with a methyl ester of a strong acid, preferably dimethyl sulfate, in the presence of an aprotic organic base such as 1,8-diazabicyclo[5.4.0]undec-7-ene (DBU). The reaction is usually carried out in an inert organic solvent, for example an amide such as dimethyl formamide, an ether such as tetrahydrofuran or a mixture thereof. The reaction temperature is conveniently from ambient temperature to 100° C.

Process variant (B) may be carried out using known hydrochlorination procedures, for example by passing gaseous HCl into a solution of the compound of formula III in an inert organic solvent, for example a hydrocarbon such as toluene. The reaction temperature is conveniently from ambient temperature to 60° C.

Compounds of formula II are novel and may be prepared by appropriate acylation of the corresponding 17-hydroxy compound, i.e. a compound of formula

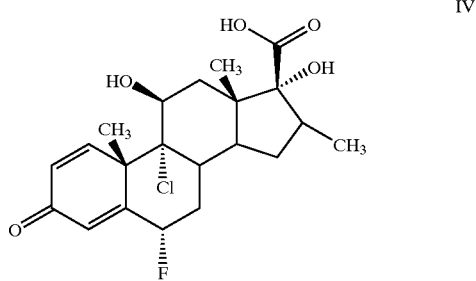

IV

The acylation may be effected using known procedures, for example by reacting a compound of formula IV with an acid halide of formula RCOX where R is as hereinbefore defined and X is halogen, such as bromine or, preferably, chlorine. The reaction is usually carried out in the presence of a base, preferably a tertiary organic base such as pyridine. The reaction temperature is suitably from ambient to 50° C. The acylation may also be effected by reacting a compound of formula IV with a carboxylic acid of formula $RCO_2H$ in the presence of an activating agent such as O-(7-azabenzotriazo-1-lyl)-N,N,N',N'-tetramethyluronium hexafluorophosphate (HATU) and a base, preferably a tertiary organic base such as N,N-diisopropylethylamine. The reaction may be carried out in a dipolar aprotic solvent, such as N,N-dimethylformamide (DMF), or a chlorohydrocarbon solvent such as dichloromethane (DCM). The reaction temperature is suitably from ambient to 60° C. Compounds of formula IV may be prepared by hydrochlorination of the corresponding 9,11-epoxy compound, of formula V

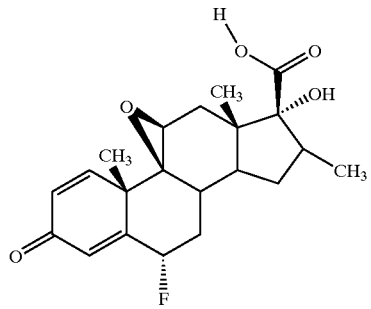

for example using known hydrochlorination procedures such as that hereinbefore described. The compound of formula V, where the 16-methyl group has the alpha conformation may be prepared as described by Aigbirhio et al, J. Labelled Compd. Radiopharm. (1997), 39(7), 567–584. The compound of formula V where the 16-methyl group has the beta conformation may be prepared as described in U.S. Pat. No. 4,607,028.

Compounds of formula III are novel and may be prepared by conversion of the corresponding 17-carboxylic acid of formula

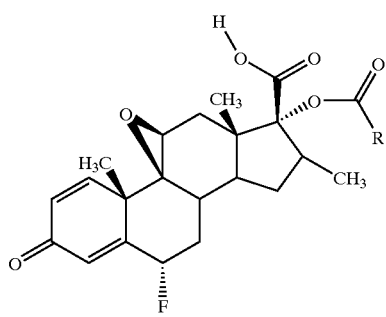

into the methyl ester thereof. This conversion may be carried out using the procedures hereinbefore described for process variant (A). Compounds of formula VI may be prepared by appropriate acylation of the corresponding 17-hydroxy compound of formula V; this acylation may be effected using known procedures, for example as hereinbefore described for acylation of compounds of formula IV.

Compounds of formula I are useful as pharmaceuticals. Accordingly, the invention also provides a compound of formula I for use as a pharmaceutical. The compounds of formula I have important pharmacological properties. For example, they have a high anti-inflammatory activity, which can be demonstrated by their inhibition of TNF-alpha synthesis and release in a human macrophage cell line and by their inhibition of inflammatory conditions, particularly in the airways, e.g. inhibition of eosinophil activation, in animal models, e.g. mouse or rat models of airways inflammation, for example as described by Szarka et al, J. Immunol. Methods (1997) 202:49–57; Renzi et al, Am. Rev. Respir. Dis. (1993) 148:932–939; Tsuyuki et al., J. Clin. Invest. (1995) 96:2924–2931; and Cemadas et al (1999) Am. J. Respir. Cell Mol. Biol. 20:1–8.

Compounds of formula I exhibit surprisingly low systemic side effects at therapeutically effective doses. Compounds of formula I have a long duration of action, with a potential for once-a-day administration.

Inhibition of TNF-alpha synthesis and release from the human macrophage cell line U937 by compounds of formula I may be demonstrated and measured in an assay as described by Sajjadi et al. J. Immunol. 1996;156:3435–3442. Compounds of Examples 3, 11, 14, 17, 19, 26, 34, 37, 39, 51, 60, 67, 72, 73, 90, 99 and 101 have $IC_{50}$ (nM) values of 0.035, 0.025, 0.100, 0.05, 0.046, 0.024, 0.10, 0.102, 0.101, 0.048, 0.048, 0.048, 0.102, 0.159, 0.076, 0.106 and 0.208 respectively in this assay.

In vivo anti-inflammatory activity may be assessed by inhibition of lung eosinophilia in rats using a modification of the method of Szarka et al op cit. Male Brown Norway rats (approximately 200 g) are sensitised on day 1 with an intraperitonial injection of 0.5 ml of a mixture of ovalbumin (0.02 mg/ml) and aluminium hydroxide (20 mg/ml), followed by Acellulare pertussis adsorbat vaccine (0.2 ml of a 1:4 dilution with 0.9% saline). The procedure is repeated on day 15 and day 21. On day 28 the test compound is administered intratracheally as a dry powder lactose blend under isoflurane anaesthesia. 24 hours later the sensitised dosed rats are exposed to an aerosol of ovalbumin (5 mg/ml) for 60 minutes and after a further 24 hours they are sacrificed. The lungs are removed and after lavage with Hank's solution (balanced salt solution, 100 ml; EDTA 100 mM, 100 ml; HPES 1M, 10 ml, water 1000 ml), eosinophil numbers in the recovered solution are quantified directly using a Corbas Helios 5Diff apparatus (Hoffman-LaRoche).

Compounds of Examples 14, 17, 26, 34, 37, 39, 51, 60, 73, 99 and 101 exhibit a reduction in eosinophil count compared to vehicle control of 65, 71, 63, 90, 61, 76, 69, 67, 43, 48 and 40% respectively in this assay. Examples 14, 26, 34 and 99 are dosed at 3 mg/kg, with the remainder at 1 mg/kg.

Systemic side effects may be assessed by reduction in thymus weight on chronic administration to rats. Male Sprague-Dawley rats (approximately 250 g) are treated once daily for 4 days with the test compound administered at a dose of 1 mg/kg either orally as a hydroxypropyl cellulose suspension or intratracheally under isoflurane anaesthesia as a dry powder lactose blend. On day 5 the rats are sacrificed, autopsy is performed and the weight of the thymus is determined. Compounds of Examples 17, 26, 34, 37, 73, 99 and 101 exhibit a reduction in thymus weight compared to vehicle control when dosed orally of 20, 2, 0, 19, 9, 0 and 2% respectively in this assay. Compounds of Examples 17, 26, 73 and 99 exhibit a reduction in thymus weight compared to vehicle control when dosed intratracheally of 78, 55, 31 and 70% respectively in this assay.

Having regard to their anti-inflammatory activity, compounds of formula I are useful in the treatment of inflammatory conditions, particularly inflammatory or obstructive airways diseases. Treatment in accordance with the invention may be symptomatic or prophylactic.

Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyper-reactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, compounds of formula I are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of formula I are also useful in the treatment of inflammatory conditions of the skin, for example psoriasis, contact dermatitis, atopic dermatitis, alopecia areata, erythema multiforma, dermatitis herpetiformis, sderoderma, vitiligo, hypersensitivity angiitis, urticaria, bullous pemphigoid, lupus erythematosus, pemphisus, epidermolysis bullosa acquisita, and other inflammatory conditions of the skin.

Compounds of formula I may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, diseases of the joints such as rheumatoid arthritis and inflammatory bowel disease such as ulcerative colitis and Crohn's disease.

Compounds of formula I are also useful as co-therapeutic agents for use in conjunction with other drug substances for treatment of airways diseases, particularly bronchodilatory or anti-inflammatory drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of formula I may be mixed with the other drug in a fixed pharmaceutical composition or it may be administered separately, before, simultaneously with or after the other drug. Such other drugs include anticholinergic or antimuscarinic agents, in particular ipratropium bromide, oxitropium bromide and tiotropium bromide, LTB4 antagonists such as those described in U.S. Pat. No. 5,451,700, LTD4 antagonists such as montelukast and zafirlukast, dopamine receptor agonists such as cabergoline, bromocriptine, ropinirole and 4-hydroxy-7-[2-[[2-[[3-(2-phenylethoxy)propyl]sulfonyl]ethyl]amino]ethyl]-2(3H)-benzothiazolone and pharmaceutically acceptable salts thereof (the hydrochloride being Viozan®—AstraZeneca), PDE4 inhibitors such as Ariflo® (GlaxoSmith Kline), Roflumilast(Byk Gulden),V-11294A(Napp), BAY19-8004 (Bayer), SCE-351591(Schering-Plough), and PD189659 (Parke-Davis) and beta-2 adrenergic receptor agonists such as salbutamol, terbutaline, salmeterol and, especially, formoterol and pharmaceutically acceptable salts thereof, and compounds (in free or salt or solvate form) of formula I of PCI International Publication No. WO00/75114, which document is incorporated herein by reference, preferably compounds of the Examples thereof, especially a compound of formula

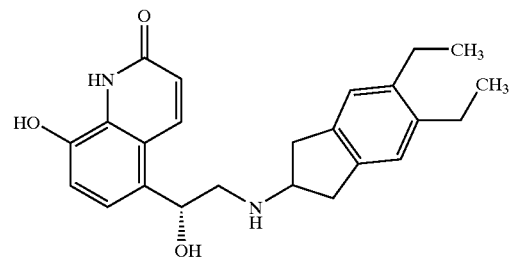

in free or pharmaceutically acceptable salt or solvate form.

Combinations of compounds of formula I and beta-2 agonists, PDE4 inhibitors or LTD4 antagonists may be used, for example, in the treatment of COPD or, particularly, asthma. Combinations of agents of the invention and anti-chofinergic or antimuscarinic agents, PDE4 inhibitors, LTB4 antagonists or dopamine agonists may be used, for example, in the treatment of astluna or, particularly, COPD.

In accordance with the foregoing, the invention also provides a method for the treatment of an inflammatory, condition, particularly an inflammatory or obstructive airways disease, which comprises administering to a subject, particularly a human subject, in need thereof an effective amount of a compound of formula I as hereinbefore described. In another aspect the invention provides the use of a compound of formula I as hereinbefore described for the manufacture of a medicament for the treatment of an inflammatory condition, particularly an inflammatory or obstructive airways disease.

The compounds of formula I may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

In a further aspect, the invention also provides a pharmaceutical composition comprising as active ingredient a compound of formula I, optionally together with a pharmaceutically acceptable diluent or carrier therefor. The composition may contain a co-therapeutic agent such as a bronchodilatory or anti-inflammatory drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

The invention includes (A) a compound of formula I in inhalable form, e.g. in an aerosol or other atomisable composition or in inhalable particulate, e.g. micronised, form, (B) an inhalable medicament comprising a compound of formula I in inhalable form; (C) a pharmaceutical product comprising a compound of formula I in inhalable form in association with an inhalation device; and () an inhalation device containing a compound of formula I in inhalable form.

Dosages of compounds of formula I employed in practising the present invention will of course vary depending, for example, on the particular condition to be treated, the effect desired and the mode of administration. In general, suitable daily dosages for administration by inhalation are of the order of 0.005 to 10 mg, while for oral administration suitable daily doses are of the order of 0.05 to 100 mg.

The invention is illustrated by the following Examples.

EXAMPLES 1–101

Compounds of formula I and their methods of preparation are shown in the following table, in which Et denotes ethyl and n-Bu denotes n-butyl, the methods being described hereinafter. In Examples Nos 34 and 45, the methyl group in the 16-postion is in the beta conformation; in all other Examples it is in the alpha conformation.

| Ex. No. | R | Method | Observed mass M+ |
|---|---|---|---|
| 1 | 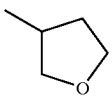 | A | 525.2 |
| 2 | 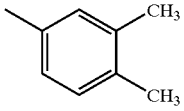 | A | 559.2 |
| 3 | 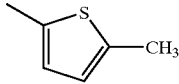 | A | 551.2 |
| 4 | 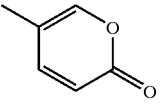 | A | 549.2 |
| 5 | 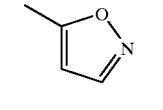 | A | 522.1 (MH+) |
| 6 | 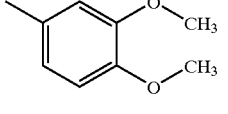 | A | 591.2 |
| 7 | 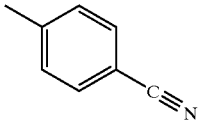 | A | 556.2 |
| 8 |  | A | 509.2 |
| 9 | 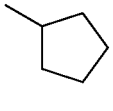 | A | 523.2 |
| 10 | 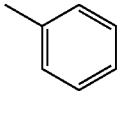 | A | 531.2 |
| 11 | 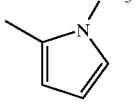 | A | 534.2 |
| 12 | 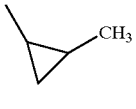 | A | 509.2 |
| 13 | 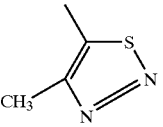 | A | 553.2 |
| 14 |  | B1 | 495.2 |
| 15 | 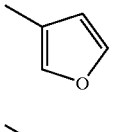 | B1 | 521.2 |
| 16 |  | B2 | 537.2 |

-continued

| Ex. No. | R | Method | Observed mass M+ |
|---|---|---|---|
| 17 | 2-furyl | B1 | 521.2 |
| 18 | 2-thienyl | B2 | 537.2 |
| 19 | 3-methyl-2-furyl | B1 | 535.2 |
| 20 | 5-bromo-2-furyl | B1 | 600.1 (MH+) |
| 21 | 3,5-dibromo-2-furyl | B1 | 679.1 (MH+) |
| 22 | 2-benzofuryl | B1 | 571.2 |
| 23 | 2-naphthyl | A | 581.4 |
| 24 | 1-methylcyclopropyl | A | 509.2 |
| 25 | tetrahydrofuran-2-yl | A | 525.2 |
| 26 | 3-methyl-2-thienyl | B2 | 551.2 |
| 27 | 2-benzothienyl | A | 587.2 |
| 28 | 5-benzofurazanyl | A | 573.3 |
| 29 | 3,4,5-trimethylisoxazol-yl | A | 550.3 |
| 30 | 1,3-dimethyl-5-pyrazolyl (N-Me) | A | 549.2 |
| 31 | 3-ethoxy-2-thienyl | A | 581.3 |
| 32 | cyclohexyl | A | 537.3 |
| 33 | 5-(methylthio)-2-thienyl | A | 583.1 |
| 34 | cyclopropyl | C | 495.3 |
| 35 | 3,5-dimethyl-2-furyl (with CH3) | A | 549.3 |
| 36 | 4-methyl-2-thienyl-5-methyl | A | 551.3 |
| 37 | 3,5-dimethylisoxazolyl | A | 536.3 |
| 38 | 1,3-dimethylpyrazolyl | A | 549.4 |
| 39 | 3,5-dimethyl-4-methyl-2-thienyl | A | 565.2 |
| 40 | 5-ethyl-2-thienyl | A | 565.3 |

-continued
| Ex. No. | R | Method | Observed mass M+ |
|---|---|---|---|
| 41 | 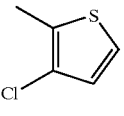 | A | 571.1 |
| 42 | 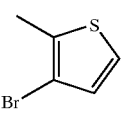 | A | 617.2 (MH+) |
| 43 | 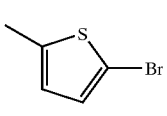 | A | 617.2 (MH+) |
| 44 | 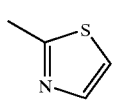 | A | 538.4 |
| 45 | 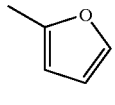 | C | 521.3 |
| 46 | 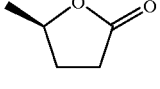 | B1 | 539.3 |
| 47 | 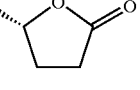 | B1 | 539.3 |
| 48 | 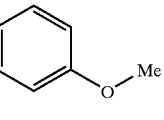 | A | 561.3 |
| 49 | 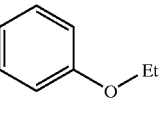 | A | 575.3 |
| 50 | 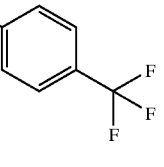 | A | 599.3 |
| 51 | 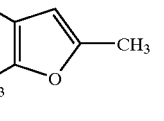 | B1 | 549.0 |
| 52 | 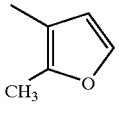 | B1 | 535.3 |
| 53 | 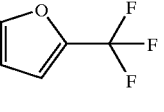 | D | 589.3 |
-continued
| Ex. No. | R | Method | Observed mass M+ |
|---|---|---|---|
| 54 | 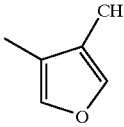 | D | 535.3 |
| 55 | 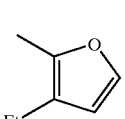 | D | 549.3 |
| 56 | 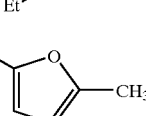 | D | 535.3 |
| 57 | 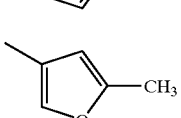 | D | 535.3 |
| 58 | 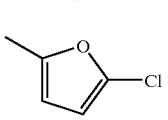 | D | 555.3 |
| 59 | 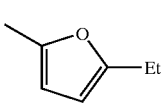 | D | 549.3 |
| 60 | 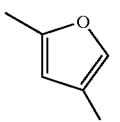 | D | 535.3 |
| 61 | 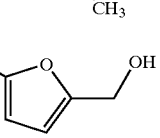 | E | 551.2 |
| 62 | 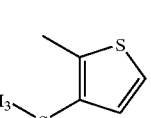 | B1 | 582.2 |
| 63 | 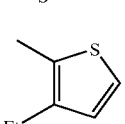 | D | 565.1 |
| 64 | 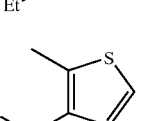 | D | 587.1 |
| 65 | 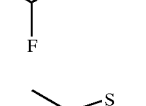 | D | 562.1 |

-continued

| Ex. No. | R | Method | Observed mass M+ |
|---|---|---|---|
| 66 | 1,2-dimethylimidazol-yl | B1 | 535.2 |
| 67 | 4-(N,N-dimethylamino)phenyl | D | 574.2 |
| 68 | 3-hydroxyphenyl | F | 547.2 |
| 69 | 4-hydroxyphenyl | F | 547.2 |
| 70 | 3-acetoxyphenyl | D | 589.2 |
| 71 | 4-acetoxyphenyl | D | 589.2 |
| 72 | 4-methylphenyl | D | 545.6 |
| 73 | 4-ethylphenyl | D | 559.6 |
| 74 | 4-isopropoxyphenyl | D | 589.7 |
| 75 | 4-chlorophenyl | D | 565.6 |
| 76 | 4-(methylamino)phenyl | D | 560.6 |

-continued

| Ex. No. | R | Method | Observed mass M+ |
|---|---|---|---|
| 77 | 4-(N-methyl-N-methylsulfonylamino)phenyl | G | 638.7 |
| 78 | 4-acetamidophenyl | D | 588.2 |
| 79 | 4-(N-methyl-N-formylamino)phenyl | D | 588.2 |
| 80 | 2-fluorophenyl | A | 549.1 |
| 81 | 2-chlorophenyl | A | 565.1 |
| 82 | 2-methylphenyl | A | 545.2 |
| 83 | 2-methoxyphenyl | A | 561.1 |
| 84 | 2-(methylthio)phenyl | A | 577.1 |
| 85 | 4-(pyrrol-1-yl)phenyl | D | 596.2 |
| 86 | 4-(methoxycarbonyl)phenyl | H | 588.5 |

-continued

| Ex. No. | R | Method | Observed mass M+ |
|---|---|---|---|
| 87 | 4-(imidazol-1-yl)phenyl-methyl | D | 597.0 |
| 88 | 4-(N-ethylamino)phenyl-methyl | D | 574.1 |
| 89 | 4-aminophenyl-methyl | I | 546.1 |
| 90 | 2-methylpyridin-yl | D | 532.27 |
| 91 | 6-chloro-2-methylpyridin-yl | D | 566.2 |
| 92 | 2,6-dimethylpyridin-yl | D | 546.3 |
| 93 | 4-methylpyridin-yl | D | 532.3 |
| 94 | 2,5-dimethylpyridin-yl | D | 546.3 |
| 95 | 3-methylpyridin-yl | D | 546.3 |
| 96 | 2-chloro-4-methylpyridin-yl | D | 566.2 |
| 97 | 5-n-butyl-2-methylpyridin-yl | D | 588.1 |
| 98 | 5-methylpyrazin-yl | D | 533.30 |
| 99 | 2,5-dimethylpyrazin-yl | D | 547.30 |
| 100 | 3-methylpyridazin-yl | D | 533.30 |
| 101 | 4-methylpyrimidin-yl | D | 533.30 |

Method A

Step 1

(6S,9S,10S,11S,13S,16R,17R)-9,11-Epoxy-6-fluoro-17-hydroxy-10,13,16-trimethyl-3-oxo-6,7,8,9,10,11,12,13,14,15,16,17-dodecahydro-3.H.-yclopenta[a]phenanthrene-17-carboxylic acid (50 g) is dissolved in dioxan (500 ML). HCl gas is bubbled through the solution for 15 minutes and the reaction mixture is stirred at room temperature. After 4 hours the resultant precipitate is collected by filtration and washed with methanol. The crude product is boiled in methanol and filtered hot. The filtrate is evaporated to provide (6S,9R,10S,11S,13S,16R,17R)-9-chloro-6-fluoro-11,17-dihydroxy-10,13,16-trimethyl-3-oxo-6,7,8,9,10,11,12,13,14,15,16,17-dodecahydro-3H-yclopenta[a]phenanthrene-17-carboxylic acid. Selected $^1$H-NMR signals (d$_6$-DMSO) δ 6.10 (1H, d), 6.30 (1H, dd), 7.25 (1H, d)

Step 2

The product of Step 1 (250 mg) is dissolved in pyridine (1.5 mL) and added to 4-methyl-1,2,3-thiadiazole-5-carbonyl chloride (108 mg). The reaction mixture is stirred at room temperature for 2 hours, then added dropwise to 6N HCl. The resultant precipitate is collected by filtration and dried, to provide 4-methyl-[1,2,3]thiadiazole-5-carboxylic acid (6S,9R,10S,11S,13S,16R,17R)-17-carboxy-9-chloro-6-fluoro-11-hydroxy-10,13,16-trimethyl-3-oxo-6,7,8,9,10,11,12,13,14,15,16,17-dodecahydro-3H-cyclopenta[a]phenanthren-17-yl ester. HPLC retention time 0.849 minutes; HPLC conditions: Zorbax High Resolution column, A=0.1% trifluoroacetic acid (TFA) in water, B=0.1% TFA in acetonitrile, gradient 30 to 95% B in A in 1 minute at 4 mL/min, 50° C.

Step 3

The product of Step 2 (326 mg) is dissolved in dimethylformamide (DMF, 0.5 mL) and tetrahydrofuran (THF, 1 mL). 1,8-Diazabicyclo[5.4.0]undec-7-ene (DBU, 101 mg) is added followed by dimethylsulphate (84 mg). The reaction mixture is stirred at room temperature for 2 hours, then partitioned between water and dichloromethane (DCM). The organic layer is dried over magnesium sulfate and evaporated. The compound is purified by flash chromatography on silica gel eluting with hexane-ethyl acetate (1:1) to afford 4-methyl-[1,2,3]thiadiazole-5-carboxylic acid (6S,9R,10S,11S,13S,16R,17R)-9-chloro-6-flouro-11-hydroxy-17-methoxycarbonyl-10,13,16-trimethyl-3-oxo-6,7,8,9,10,11,12,13,14,15,16,17-dodecahydro-3H-cyclopenta[a]phenanthren-17-yl ester.

Method B1

Step 1

(6S,9S,10S,11S,13S,16R,17R)-9,11-Epoxy-6-fluoro-17-hydroxy-10,13,16-trimethyl-3-oxo-6,7,8,9,10,11,12,13,14,15,16,17-dodecahydro-3H-cyclopenta[a]phenanthrene-17-carboxylic acid (5 g) is dissolved in pyridine (15 mL) and cooled to 0° C. 2-Furoyl chloride (1.82 g) is added and the reaction mixture is stirred at room temperature. After 2 hours, the reaction mixture is added dropwise to a vigorously stirred solution of 6M HCl. DCM is added, the phases are separated and the organic phase is washed with water and brine. After drying over magnesium sulphate, evaporation affords furan-2-carboxylic acid (6S,9S,10S,11S,13S,16R,17R)-9,11-epoxy-6-fluoro-17-carboxy-10,13,16-trimethyl-3-oxo-6,7,8,9,10,11,12,13,14,15,16,17-dodecahydro-3H-cyclopenta[a]phenanthren-17-yl ester. Selected $^1$H-NMR signals (CDCl$_3$) δ 6.30 (1H, dd), 6.5 (2H, m), 6.55 (1H, d), 7.20–7.65 (m, 2H).

Step 2

The product of Step 1 (6.20 g) is dissolved in ethyl acetate (100 mL). DBU (2.20 g) and dimethyl sulphate (1.83 g) are added sequentially. The reaction mixture is stirred at room temperature for 2 hours, then partitioned between ethyl acetate and water. The organic layer is washed with water and brine, dried over magnesium sulphate and evaporated. Crystallisation from methanol affords furan-2-carboxylic acid (6S,9S,10S,11S,13S,16R,17R)-9,11-epoxy-6-fluoro-17-methoxycarbonyl-10,13,16-trimethyl-3-oxo-6,7,8,9,10,11,12,13,14,15,16,17-dodecahydro-3H-cyclopenta[a]phenanthren-17-yl ester. Selected $^1$H-NMR signals (CDCl$_3$) δ 3.75 (3H, s), 6.30 (1H, dd), 6.45 (1H, d), 6.55 (2H, m), 7.15 (1H, d), 7.60 (1H, d).

Step 3

The product of Step 2 (4.5 g) is dissolved in toluene (150 mL). HCl gas is bubbled through the solution for 15 minutes and the reaction mixture is stirred at room temperature for 6 hours. The solvent is evaporated and the crude product crystallised from isopropanol to yield furan-2-carboxylic acid (6S,9R,10S,11S,13S,16R,17R)-9-chloro-6-fluoro-11-hydroxy-17-methoxycarbonyl-10,13,16-trimethyl-3-oxo-6,7,8,9,10,11,12,13,14,15,16,17-dodecahydro-3H-cyclopenta[a]phenanthren-17-yl ester.

Method B2

Step 1

(6S,9S,10S,11S,13S,16R,17R)-9,11-Epoxy-6-fluoro-17-hydroxy-10,13,16-trimethyl-3-oxo-6,7,8,9,10,11,12,13,14,15,16,17-dodecahydro-3H-cyclopenta[a]phenanthrene-17-carboxylic acid (20 g) is dissolved in pyridine (50 mL) and cooled to 0° C. 3-Methylthiophene-2-carbonyl chloride (9.39 g) is added and the reaction is stirred at room temperature. After 2 hours, the reaction mixture is added dropwise to a vigorously stirred solution of 6M HCl. DCM is added, the phases are separated and the organic phase is washed with water and brine. After drying over magnesium sulphate, evaporation is followed by flash column chromatography on silica gel eluting with DCM-methanol (25:1) to afford 3-methylthiophene-2-carboxylic acid (6S,9S,10S,11S,13S,16R,17R)-9,11-epoxy-6-fluoro-17-carboxy-10,13,16-trimethyl-3-oxo-6,7,8,9,10,11,12,13,14,15,16,17-dodecahydro-3H-cyclopenta[a]phenanthren-17-yl ester. Selected $^1$H-NMR signals (CDCl$_3$) δ 0.90 (3H, d), 0.95 (3H, s), 1.40 (3H, s), 2.40 (3H, s).

Step 2

The product of Step 1 (11.1 g) is dissolved in ethyl acetate (200 mL). DBU (4.05 g) and dimethyl sulphate (3.36 g) are added sequentially and the reaction mixture is stirred at room temperature for 2 hours, then partitioned between ethyl acetate and water. The organic layer is washed with water and brine, dried over magnesium sulphate and evaporated. Crystallisation from methanol affords 3-methylthiophene-2-carboxylic acid (6S,9S,10S,11S,13S,16R,17R)-9,11-epoxy-6-fluoro-17-methoxycarbonyl-10,13,16-trimethyl-3-oxo-6,7,8,9,10,11,12,13,14,15,16,17-dodecahydro-3H-cyclopenta[a]phenanthren-17-yl ester. Selected $^1$H-NMR signals (CDCl$_3$) δ 0.90 (3H, d), 0.92 (3H, s), 1.40 (3H, s), 2.40 (3H, s), 3.65 (3H, s).

Step 3

The product of Step 2 (16 g) is dissolved in toluene (250 mL). HCl gas is bubbled through the solution for 15 minutes and the reaction mixture is stirred at room temperature for 16 hours. The solvent is evaporated and the crude product crystallised first from acetonitrile and secondly from isopropanol to afford 3-methylthiophene-2-carboxylic acid (6S,9R,10S,11S,13S,16R,17R)-9-chloro-6-fluoro-11-hydroxy-17-methoxycarbonyl-10,13,16-trimethyl-3-oxo-6,7,8,9,10,11,12,13,14,15,16,17-dodecahydro-3H-cyclopenta[a]phenanthren-17-yl ester.

Method C

Step 1

(6S,9S,10S,11S,13S,16S,17R)-9,11-Epoxy-6-fluoro-17-hydroxy-10,13,16-trimethyl-3-oxo-6,7,8,9,10,11,12,13,14,15,16,17-dodecahydro-3H-cyclopenta[a]phenanthrene-17-carboxylic acid (1 g) is dissolved in pyridine (5 mL). Cyclopropylcarbonyl chloride (330 mg) is added and the reaction mixture stirred at room temperature. After 2 hours the solution is added dropwise to a vigorously stirred solution of 6M HCl. The resultant precipitate is collected by filtration and dried to yield (6S,9S,10S,11S,13S,16S,17R)-9,11-epoxy-17-cyclopropanecarbonyloxy-6-fluoro-10,13,16-trimethyl-3-oxo-6,7,8,9,10,11,12,13,14,15,16,17-dodecahydro-3H-yclopenta[a]phenanthrene-17-carboxylic acid. Selected $^1$H-NMR signals (CDCl$_3$) d 6.25 (1H, dd), 6.45 (1H, d), 6.55 (1H, d).

Step 2

The product of Step 1 (1.1 g) is dissolved in ethyl acetate (25 mL). DBU (450 mg) is added followed by dimethyl sulphate (370 mg). The reaction is stirred at room temperature for 2 hours and then partitioned between ethyl acetate and water. The organic layer is washed with water and brine, dried over magnesium sulfate and evaporated. The crude product is crystallised from methanol to provide (6S,9S,10S,11S,13S,16S,17R)-9,11-epoxy-17-cyclopropanecarbonyloxy-6-fluoro-10,13,16-trimethyl-3-oxo-6,7,8,9,10,11,12,13,14,15,16,17-dodecahydro-3H-cyclopenta[a]phenanthrene-17-carboxylic acid methyl ester. Selected H-NMR signal (CDCl$_3$) δ 3.65 (3H, s), 6.25 (1H, dd), 6.45 (1H, d), 6.55 (1H, d).

Step 3

The product of Step 2 (500 mg) is dissolved in toluene (20 mL). HCl gas is bubbled through the solution for 5 minutes and the reaction mixture is stirred at room temperature for 18 hours. The solvent is evaporated and the crude product crystallised from isopropanol-methanol to afford (6S,9R,10S,11S,13S,16S,17R)-9-chloro-17-cyclopropanecarbonyloxy-6-fluoro-11-hydroxy-10,13,16-trimethyl-3-oxo-6,7,8,9,10,11,12,13,14,15,16,17-dodecahydro-3H-cyclopenta[a]phenanthrene-17-carboxylic acid methyl ester.

Method D

Step 1

N,N-Diisopropylethylamine (2.3 mL) is added to a cooled (0° C.) solution of 5-methylpyrazine-2-carboxylic acid (736 mg) in DMF (7 mL), followed by O-(7-azabenzotriazo-1-lyl)-N,N,N',N'-tetramethyluronium hexafluorophosphate (HATU, 2.26 g). The suspension is stirred at room temperature for 10 minutes, then a solution of (6S,9S,10S,11S,13S,16R,17R)-9,11-epoxy-6-fluoro-17-hydroxy-10,13,16-trimethyl-3-oxo-6,7,8,9,10,11,12,13,14,15,16,17-dodecahydro-3H-cyclopenta[a]phenanthrene-17-carboxylic acid (2 g) in DMF (7 ml) is added. After 2 hours, the reaction mixture is added dropwise to a solution of 1M HCl. The product is collected by filtration, washed repeatedly with water and dried to yield 5-methyl-pyrazine-2-carboxylic acid (6S,9S,10S,11S,13S,16R,17R)-9,11-epoxy-6-fluoro-17-carboxy-10,13,16-trimethyl-3-oxo-6,7,8,9,10,11,12,13,14,15,16,17-dodecahydro-3H-cyclopenta[a]phenanthren-17-yl ester. Selected H-NMR signals (CDCl₃) δ 0.95 (3H, d), 1.10 (3H, s) 1.40 (3H, s), 2.65 (3H, s).

Step 2

The product of Step 1 (2.50 g) is dissolved in DMF (11 mL) and cooled to 0° C. DBU (1.68 g) is added, followed by dimethyl sulphate (953 mg) after 10 minutes. The reaction is stirred at room temperature for 2 hours, poured into water and extracted with ethyl acetate. The combined organic phases are washed with water and brine, then dried over sodium sulfate. Evaporation affords 5-methylpyrazine-2 carboxylic acid (6S,9S,10S,11S,13S,16R,17R)-9,11-epoxy-6-fluoro-17-methoxycarbonyl-10,13,16-trimethyl-3-oxo-6,7,8,9,10,11,12,13,14,15,16,17-dodecahydro-3H-cyclopenta[a]phenanthren-17-yl ester. Observed mass (M+H) 511.

Step 3

The product of Step 2 (1.92 g) is dissolved in toluene (100 mL). HCl gas is bubbled through the solution for 90 minutes and the reaction mixture is stirred at room temperature for 16 hours. The solvent is evaporated, the crude product triturated with hot ethanol and dried to afford 5-methylpyrazine-2-carboxylic acid 6S,9R,10S,11S,13S,16R,17R)-9-chloro-6-flouro-11-hydroxy-17-methoxycarbonyl-10,13,16-trimethyl-3-oxo-6,7,8,9,10,11,12,13,14,15,16,17-dodecahydro-3H-cyclopenta[a]phenanthren-17-yl ester.

Method E

Step 1

N,N-Diisopropylethylamine (0.508 mL) is added to a cooled (0° C.) solution of 5-acetoxyfuran-2-carboxylic add (258 mg) in DMF (1 mL), followed by HATU (556 mg). The suspension is stirred at room temperature for 10 minutes, then a solution of (6S,9S,10S,11S,13S,16R,17R)-9,11-epoxy-6-fluoro-17-hydroxy-10,13,16-trimethyl-3-oxo-6,7,8,9,10,11,12,13,14,15,16,17-dodecahydro-3H-cyclopenta[a]phenanthrene-17-carboxylic acid (500 mg) in DMF (1 mL) is added. After 2 hours, the reaction mixture is added slowly to a solution of 0.2M HCl and extracted with DCM. The organic phase is washed with water and brine, then dried over magnesium sulfate and evaporated to afford 5-acetoxyfuran-2-carboxylic acid (6S,9S,10S,11S,13S,16R,17R)-9,11-epoxy-6-fluoro-17-carboxy-10,13,16-trimethyl-3-oxo-6,7,8,9,10,11,12,13,14,15,16,17-dodecahydro-3H-cyclopenta[a]phenanthren-17-yl ester. TLC $R_f$ 0.5 (10:1 DCM-methanol elution)

Step 2

The product of Step 1 (721 mg) is dissolved in ethyl acetate (25 mL). DBU (242 mg) is added, followed by dimethyl sulfate (201 mg) and the reaction is stirred at room temperature for 2 hours, then diluted with 0.2 M HCl. The organic phase is washed with water and brine, then dried over magnesium sulfate and evaporated. Purification by flash chromatography on silica gel eluting with hexanes-ethyl acetate (2:1) affords 5-acetoxyfuran-2-carboxylic acid (6S,9S,10S,11S,13S,16R,17R)-9,11-epoxy-6-fluoro-17-methoxycarbonyl-10,13,16-trimethyl-3-oxo-6,7,8,9,10,11,12,13,14,15,16,17-dodecahydro-3H-cyclopenta[a]phenanthren-17-yl ester. Selected NMR signals (CDCl₃) δ 0.96 (3H, d), 0.98 (3H, s), 1.40 (3H, s), 2.18 (3H, s), 2.76 (3H, s).

Step 3

The product of Step 2 (555 mg) is dissolved in methanol (10 mL) and 2M methanolic sodium hydroxide (1 mL) is added. After 1 hour the solvent is evaporated and the residue partitioned between water and ethyl acetate. The organic phase is dried over magnesium sulfate and evaporated. Purification by flash chromatography eluting with hexanes-ethyl acetate (1:1) affords 5-hydroxyfuran-2-carboxylic acid (6S,9S,10S,11S,13S,16R,17R)-9,11-epoxy-6-fluoro-17-methoxycarbonyl-10,13,16-trimethyl-3-oxo-6,7,8,9,10,11,12,13,14,15,16,17-dodecahydro-3H-cyclopenta[a]phenanthren-17-yl ester. TLC $R_f$ 0.25 (1:1 hexane-ethyl acetate elution).

Step 4

The product of Step 3 (250 mg) is dissolved in toluene (10 mL) and dioxan (10 mL). HCl gas is bubbled through the solution for 10 minutes and the reaction mixture stirred at room temperature for 16 hours. The solvent is evaporated and the crude product purified by flash column chromatography on silica gel, eluting with hexane-ethyl acetate (1:1), then triturated with ether to afford 5-hydroxyfuran-2-carboxylic acid (6S,9R,10S,11S,13S,16R,17R)-9-chloro-6-fluoro-11-hydroxy-17-methoxycarbonyl-10,13,16-trimethyl-3-oxo-6,7,8,9,10,11,12,13,14,15,16,17-dodecahydro-3H-cyclopenta[a]phenanthren-17-yl ester.

Method F

Step 1

(6S,9S,10S,11S,13S,16R,17R)-9,11-epoxy-6-fluoro-17-hydroxy-10,13,16-trimethyl-3-oxo-6,7,8,9,10,11,12,13,14,15,16,17-dodecahydro-3H-cyclopenta[a]phenanthrene-17-carboxylic acid is converted, by a process analogous to Step 1 of Method D, to 3-acetoxy-benzoic acid (6S,9S,10S,11S,13S,16R,17R)-9,11-epoxy-6-fluoro-17-carboxy-10,13,16-trimethyl-3-oxo-6,7,8,9,10,11,12,13,14,15,16,17-dodecahydro-3H-cyclopenta[a]-phenanthren-17-yl ester. HPLC retention time 0.762 minutes, conditions as for Method A.

Step 2

The product of Step 1 is converted, by a process analogous to Step 2 of Method D, to 3-acetoxybenzoic acid (6S,9S,10S,11S,13S,16R,17R)-9,11-epoxy-6-fluoro-17-methoxycarbonyl-10,13,16-trimethyl-3-oxo-6,7,8,9,10,11,12,13,14,15,16,17-dodecahydro-3H-cyclopenta[a]phenanthren-17-yl ester. Observed mass 552 (M+).

Step 3

The product of Step 2 converted, by a process analogous to Step 3 of Method E, to 3-hydroxybenzoic acid (6S,9S,10S,11S,13S,16R,17R)-9,11-epoxy-fluoro-17-methoxycarbonyl-10,13,16-trimethyl-3-oxo-6,7,8,9,10,11,12,13,14,15,16,17-dodecahydro-3H-yclopenta[a]phenanthren-17-yl ester. Observed mass 510 (M+).

Step 4

The product of Step 3 is converted, by a process analogous to Step 4 of Method E, to 3-hydroxybenzoic acid (6S,9R,10S,11S,13S,16R,17R)-9-chloro-6-fluoro-11-hydroxy-17-methoxycarbonyl-10,13,16-trimethyl-3-oxo-6,7,8,9,10,11,12,13,14,15,16,17-dodecahydro-3H-cyclopenta[a]phenanthren-17-yl ester.

Method G

Step 1

(6S,9S,10S,11S,13S,16R,17R)-9,11-epoxy-6-fluoro-17-hydroxy-10,13,16-trimethyl-3-oxo-6,7,8,9,10,11,12,13,14,15,16,17-dodecahydro-3H-clopenta[a]phenanthrene-17-carboxylic acid is converted, by a process analogous to Step 1 of Method D, to 4-methylaminobenzoic acid (6S,9S,10S,11S,13S,16R,17R)-9,11-epoxy-6-fluoro-17-caboxy-10,13,16-trimethyl-3-oxo-6,7,8,9,10,11,12,13,14,15,16,17-dodecahydro-3H-cyclopenta[a]phenanthren-17-yl ester. HPLC retention time 0.728 minutes, conditions Max RP High Resolution column, A=0.05% TFA in water, B=0.105% TFA in acetonitrile, gradient 30 to 95% B in A in 1 minute at 4 mL/min, 50° C.

Step 2

The product of Step 1 is converted, by a process analogous to Step 2 of Method D, to 4-methylaminobenzoic acid (6S,9S,10S,11S,13S,16R,17R)-9,11-epoxy-6-fluoro-17-methoxycarbonyl-10,13,16-trimethyl-3-oxo-6,7,8,9,10,11,12,13,14,15,16,17-dodecahydro-3H-cyclopenta[a]phenanthren-17-yl ester. Observed mass 523 (M+).

Step 3

The product of Step 2 (42 mg) is dissolved in DCM (1 mL) and DBU (66 mg) is added, followed 5 minutes later by methanesulfonyl chloride (114 mg). The reaction is heated to reflux overnight, after which the solvent is evaporated and the residue is taken into DMF. The solution is added dropwise to 1M HCl and the resultant solid collected by filtration and dried to afford 4-(methanesulfonylmethylamino)benzoic acid (6S,9S,10S,11S,13S,16R,17R)-9,11-epoxy-6-fluoro-17-methoxycarbonyl-10,13,16-trimethyl-3-oxo-6,7,8,9,10,11,12,13,14,15,16,17-dodecahydro-3H-cyclopenta[a]phenanthren-17-yl ester. Observed mass 601 (M+).

Step 4

The product of Step 3 (35 mg) is dissolved in toluene (10 mL) and HCl gas is bubbled through the solution for 5 mins, prior to stirring at room temperature for 16 hours. The resultant solid is collected by filtration and dried to afford 4-(methanesulfonylmethylamino)-benzoic acid (6S,9R,10S,11S,13S,16R,17R)-9-chloro-6-fluoro-11-hydroxy-17-methoxycarbonyl-10,13,16-trimethyl-3-oxo-6,7,8,9,10,11,12,13,14,15,16,17-dodecahydro-3H-cyclopenta[a]phenanthren-17-yl ester.

Method H

Step 1

Sodium hydride (60% dispersion in mineral oil, 241 mg) is added to a suspension of terephthalic acid (1 g) in DMF (5 mL), followed after 5 mins by 2-trimethylsilyl)ethoxymethyl chloride (0.998 g). After 2 hours, the reaction is added dropwise to water and the resultant solid collected by filtration and dried. Purification by flash column chromatography on silica gel, eluting with ethyl acetate affords terephthalic acid mono-(2-trimethylsilylethoxymethyl) ester. HPLC retention time 0.879 minutes, conditions as for Method G.

Step 2

(6S,9S,10S,11S,13S,16R,17R)-9,11-epoxy-6-fluoro-17-hydroxy-10,13,16-trimethyl-3-oxo-6,7,8,9,10,11,12,13,14,15,16,17-dodecahydro-3H-cyclopenta[a]phenanthrene-17-carboxylic acid is converted, by a process analogous to Step 1 of Method D, to terephthalic acid mono-(2-trimethylsilylethoxymethyl) ester (6S,9S,10S,11S,13S,16R,17R)-9,11-epoxy-6-fluoro-17-carboxy-10,13,16-trimethyl-3-oxo-6,7,8,9,10,11,12,13,14,15,16,17-dodecahydro-3H-cyclopenta[a]phenanthren-17-yl ester. HPLC retention time 1.046 minutes, conditions as for Method G.

Step 3

The product of Step 2 converted, by a process analogous to Step 2 of Method D, to trimethylsilylethoxymethyl) ester (6S,9S,10S,11S,13S,16R,17R)-9,11-epoxy-6-fluoro-17-methoxycarbonyl-10,13,16-trimethyl-3-oxo-6,7,8,9,10,11,12,13,14,15,16,17-dodecahydro-3H-cyclopenta[a]phenanthren-17-yl ester. IPLC retention time 1.055 minutes, conditions as for Method G.

Step 4

The product of Step 3 (320 mg) is dissolved in toluene (10 mL) and HCl gas is bubbled through the solution for 5 minutes, prior to stirring at room temperature for 16 hours. The resultant solid is collected by filtration, triturated with DCM and dried to afford terephthalic acid (6S,9R,10S,11S,13S,16R,17R)-9-chloro-6-fluoro-11-hydroxy-17-methoxycarbonyl-10,13,16-trimethyl-3-oxo-6,7,8,9,10,11,12,13,14,15,16,17-dodecahydro-3H-cyclopenta[a]phenanthren-17-yl monoester. Observed mass 575.1 (M+).

Step 5

The product of Step 4 (24 mg) is dissolved in DMF (0.5 mL). DBU (8 mg) is added, followed by DMS (7 mg) and the reaction is stirred at room temperature for 1 hour. The reaction mixture is added dropwise to 1M HCl and the resultant solid collected by filtration and dried to afford terephthalic acid 1-methyl-4-[(6S,9S,10S,11S,13S,16R,17R)-9,11-epoxy-6-flouro-17-methoxycarbonyl-10,13,16-trimethyl-3-oxo-6,7,8,9,10,11,12,13,14,15,16,17-dodecahydro-3H-cyclopenta[a]phenanthren-17-yl] ester.

Method I

Step 1

(6S,9S,10S,11S,13S,16R,17R)-9,11-epoxy-6-fluoro-17-hydroxy-10,13,16-trimethyl-3-oxo-6,7,8,9,10,11,12,13,14,15,16,17-dodecahydro-3.H.-cyclopenta[a]phenanthrene-17-carboxylic acid is converted, by a process analogous to Step 1 of Method D, to 4-(tert-butoxycarbonylamino)benzoic acid (6S,9S,10S,11S,13S,16R,17R)-9,11-epoxy-6-fluoro-17-carboxy-10,13,16-trimethyl-3-oxo-6,7,8,9,10,11,12,13,14,15,16,17-dodecahydro-3H-cyclopenta[a]phenanthren-17-yl ester. HPLC retention time 0.873 minutes, conditions as for Method G.

Step 2

The product of Step 1 is converted, by a process analogous to Step 2 of Method D, to 4-(tert-butoxycarbonylamino)benzoic acid (6S,9S,10S,11S,13S,16R,17R)-9,11-epoxy-6-fluoro-17-methoxycarbonyl-10,13,16-trimethyl-3-oxo-6,7,8,9,10,11,12,13,14,15,16,17-dodecahydro-3H-cyclopenta[a]phenanthren-17-yl ester. Observed mass 609.7 (M+).

Step 3

The product of Step 2 (510 mg) is dissolved in 150 mL of toluene and HCl gas is bubbled through the solution for 5 mins, prior to stirring at room temperature for 48 hours. The solvent is evaporated and the crude product crystallised from ethyl acetate-cyclohexane to afford 4-aminobenzoic acid (6S,9R,10S,11S,13S,16R,17R)-9-chloro-6-fluoro-11-hydroxy-17-methoxycarbonyl-10,13,16-trimethyl-3-oxo-6,7,8,9,10,11,12,13,14,15,16,17-dodecahydro-3H-cyclopenta[a]phenanthren-17-yl monoester.

What is claimed is:

1. A compound of formula

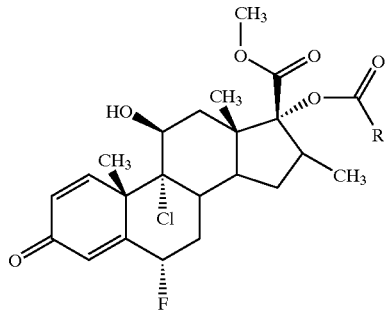

where R is a monovalent cyclic organic group having from 3 to 15 atoms in the ring system.

2. A compound according to claim 1, in which R is $C_3$–$C_6$-cycloalkyl.

3. A compound according to claim 1, in which R is an at least partially saturated heterocyclic group having 5 to 10 ring atoms, of which one or more are ring hetero atoms selected from nitrogen, oxygen and sulfur.

4. A compound according to claim 3, in which R is a 5-membered heterocyclic group having one ring hetero atom.

5. A compound according to claim 1, in which R is phenyl or naphthyl optionally substituted by one or more substituents selected from halogen, hydroxyl, $C_1$–$C_4$-acyloxy, cyano, $C_1$–$C_4$-alkyl, halo-$C_1$–$C_4$-alkyl, $C_1$–$C_4$-alkoxy, amino, $C_1$–$C_4$-alkylamino, di-($C_1$–$C_4$-alkyl)amino, $C_1$–$C_4$-acylamino, $C_1$–$C_4$-acyl($C_1$–$C_4$ alkyl)amino, $C_1$–$C_4$-alkylsulfonyl($C_1$–$C_4$-alkyl)amino, $C_1$–$C_4$ alkoxycarbonyl, $C_1$–$C_4$-alkylthio, or 5-membered N-heterocyclyl.

6. A compound according to claim 1, in which R is a heterocyclic aromatic group having a 5-membered heterocyclic ring with one, two or three ring hetero atoms selected from nitrogen, oxygen and sulfur, the heterocyclic ring being unsubstituted or substituted by one or two substituents selected from halogen, $C_1$–$C_4$-alkyl, halo-$C_1$–$C_4$-alkyl, $C_1$–$C_4$-alkoxy, $C_1$–$C_4$-alkylthio, cyano or hydroxy-$C_1$–$C_4$-alkyl, and the heterocyclic ring being optionally fused to a benzene ring.

7. A compound according to claim 1, in which R is a heterocyclic aromatic group having a 6-membered heterocyclic ring with one or two ring nitrogen atoms, the heterocyclic ring being unsubstituted or substituted by one or two substituents selected from halogen, cyano, hydroxyl, $C_1$–$C_4$-acyloxy, amino, $C_1$–$C_4$ alkylamino, di-($C_1$–$C_4$-alkyl)amino, $C_1$–$C_4$-alkyl, hydroxy-$C_1$–$C_4$-alkyl, halo-$C_1$–$C_4$-alkyl $C_1$–$C_4$-alkoxy, or $C_1$–$C_4$-alkylthio and the heterocyclic ring being optionally fused to a benzene ring.

8. A compound of formula I

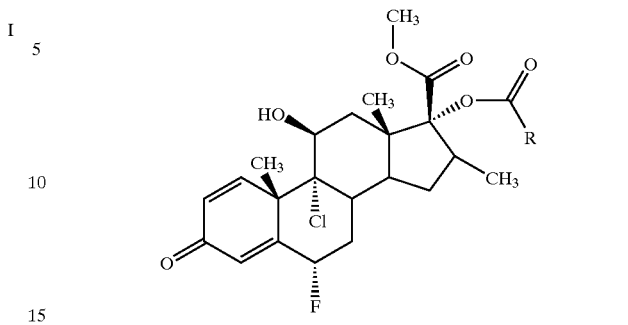

where the indicated 16-methyl group has the alpha conformation and R is 5-methyl-2-thienyl, N-methyl-2-pyrrolyl, cyclopropyl, 2-furyl, 3-methyl-2-furyl, 3-methyl-2-thienyl, 5-methyl-3-isoxazolyl, 3,5-dimethyl-2-thienyl, 2,5-dimethyl-3-furyl, 4-methyl-2-furyl, 4-(dimethylamino) phenyl, 4-methylphenyl, 4-ethylphenyl, 2-pyridyl, 4-pyrimidyl or 5-methyl-2-pyrazinyl or the indicated 16-methyl group has the beta conformation and R is cyclopropyl.

9. A compound according to claim 1 in which R contains a basic group and the compound is in the form of an acid addition salt.

10. A composition comprising a compound according to claim 1 in combination with another drug substance which is a bronchodilator or anti-inflammatory, particularly a beta-2 adrenergic receptor agonist.

11. A pharmaceutical composition comprising as active ingredient a compound according to claim 1, optionally together with a pharmaceutically acceptable diluent or carrier therefor.

12. A process for the preparation of compounds of formula I as defined claim 1 which comprises (A) conversion of a carboxylic acid of formula

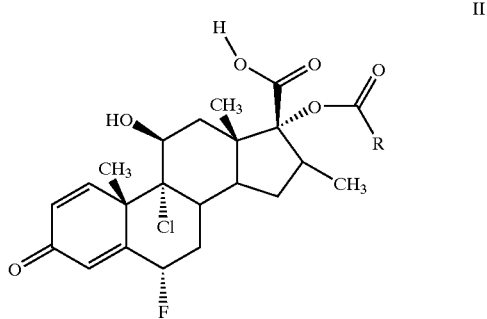

where R is a monovalent cyclic organic group, or an ester-forming functional derivative thereof, into the methyl ester thereof; or (B) hydrochlorination of a compound of formula

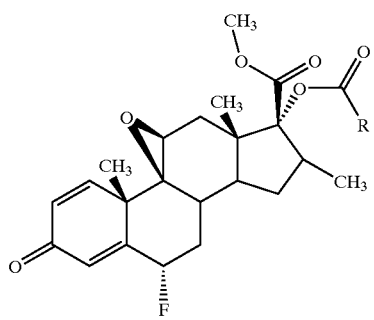

III where R is a monovalent cyclic organic group.

13. A compound of formula II or III as defined in claim 12.

14. A composition comprising a compound according to claim 8 in combination with another drug substance which is a bronchodilator or anti-inflammatory, particularly a beta-2 adrenergic receptor agonist.

15. A method of treating an inflammatory condition in a subject in need of such treatment, which comprises administering to said subject an effective amount of a compound of formula I as defined in claim 1 in free form or in the form of a pharmaceutically acceptable salt.

16. A method of treating an inflammatory condition in a subject in need of such treatment, which comprises administering to said subject an effective amount of a compound of formula I as defined in claim 6 in free form or in the form of a pharmaceutically acceptable salt.

17. A method of treating an inflammatory condition in a subject in need of such treatment, which comprises administering to said subject an effective amount of a compound of formula I as defined in claim 8 in free form or in the form of a pharmaceutically acceptable salt.

18. A method according to claim 15, wherein the inflammatory condition is an airways disease.

19. A pharmaceutical composition comprising as active ingredient a compound according to claim 6, optionally together with a pharmaceutically acceptable diluent or carrier therefor.

20. A pharmaceutical composition comprising as active ingredient a compound according to claim 8, optionally together with a pharmaceutically acceptable diluent or carrier therefor.

* * * * *